United States Patent [19]

Imahori et al.

[11] Patent Number: 5,001,055

[45] Date of Patent: Mar. 19, 1991

[54] PROCESS FOR PRODUCING PHYSIOLOGICALLY ACTIVE SUBSTANCE

[75] Inventors: Kazutomo Imahori, Tokyo; Isao Tomioka, Kyoto; Hiroshi Nakajima, Kyoto; Senji Kitabatake, Kyoto, all of Japan

[73] Assignee: Unitika Ltd., Hyogo, Japan

[21] Appl. No.: 862,731

[22] Filed: May 13, 1986

[30] Foreign Application Priority Data

May 13, 1985 [JP] Japan .................. 60-103150
May 13, 1985 [JP] Japan .................. 60-103151

[51] Int. Cl.$^5$ .................. C12P 39/00; C12P 1/00; C12P 19/30; C12Q 3/00
[52] U.S. Cl. .................. 435/42; 435/41; 435/89; 435/92; 435/3; 435/813
[58] Field of Search .................. 435/41, 42, 3, 89, 92, 435/109, 175, 813

[56] References Cited

FOREIGN PATENT DOCUMENTS 1194825 10/1985 Canada .................. 435/92
0084975 8/1983 European Pat. Off. .
0146265 6/1985 European Pat. Off. .

OTHER PUBLICATIONS

Pollock et al, "Large-Scale Enzymatic Synthesis with Cofactor Regeneration: Glucose-6-Phosphate", J. Am. Chem. Soc. 99, 2366-2367, 1977.

Kondo et al, "Construction of a System for the Regeneration of Adenosine-5'-Triphosphate, Which Supplies Energy to Bioreactor", J. Applied Biochemistry, 1984, vol. 6, 29-38.

*Primary Examiner*—Charles F. Warren
*Assistant Examiner*—Gail Poulos
*Attorney, Agent, or Firm*—Sughrue, Mion, Zinn, Macpeak & Seas

[57] ABSTRACT

A process for producing a physiologically active substance by a combined enzymatic method is disclosed. In the combined enzymatic method, a reactant solution containing a precursor or precursors for the physiologically active substance, AXP, and a divalent metal ion is supplied at one end of a reactor incorporating either the combined enzymatic reaction system (a) or (b), wherein (a) is a reaction system including an enzyme for converting AMP to ADP, an enzyme for converting ADP to ATP, and an enzyme which catalyzes the synthesis of the physiologically active substance as it converts ATP to AMP; and (b) is a reaction system including an enzyme for converting ADP to ATP and an enzyme which catalyzes the synthesis of the physiologically active substance as it converts ATP to ADP, wherein the concentration of the divalent metal ion supplied into the reactor is held at a level no higher than 30 mM while the concentration of the AXP is held below that of that of the precursor or precursors for the physiologically active substance, and the physiologically active substance produced is withdrawn from the other end of the reactor.

6 Claims, No Drawings

PROCESS FOR PRODUCING PHYSIOLOGICALLY ACTIVE SUBSTANCE

FIELD OF THE INVENTION

The present invention relates to a process for producing a physiologically active substance by a combined enzymatic reaction using adenosine-5'-triphosphate as an energy source or a cofactor.

BACKGROUND OF THE INVENTION

With the recent reappraisal of the current state of the chemical industry, chemical reactions which take place in living bodies are drawing attention and active efforts are being made in order to reproduce such chemical reactions within reactors at chemical plants, rather than in living bodies. Many enzyme-catalyzed biosynthetic reactions are carried out in living bodies in order to support life and the capability of reproducing such biosynthetic reactions within reactors is becoming an essential technology in the chemical industry because, for one thing, it readily provides those compounds which are difficult to produce by synthetic chemical reactions and, for another, it satisfies society's needs for energy conservation and a clean environment. This technology has already been commercialized in the fields of hydrolysis and isomerization.

One of the most important biosynthetic reactions is the binding reaction, and in order to carry out this reaction, adenosine-5'-triphosphate (hereinafter abbreviated as ATP) is necessary as an energy source or a cofactor. After acting as an energy source or a cofactor, ATP is degraded to adenosine-5'-diphosphate (ADP) or adenosine-5'-monophosphate (AMP). Industrial reproduction of the binding reaction therefore requires that ATP be supplied at low cost. However, ATP is a very expensive substance and the key point in the effort to commercialize the reproduction of the binding reaction is to regenerate ATP after it has been consumed into the form of ADP or AMP. In particular, successful commercialization of the binding reaction in chemical reactors will depend on converting the "lowest energy" AMP to ATP.

In fact, however, not many cases have been known of the reproduction of substances by the binding reaction as it is accompanied by ATP regeneration. One approach which has been proposed is to regenerate or replenish the consumed ATP by utilizing microbial glycolysis, and an attempt was made to use AMP as the starting material for the production of ATP (see, for example, S. Tochikura et al., *Yuki Gosei Kagaku Kyokai Shi*, Vol. 39, No. 6, p. 487, 1981). The AMP used in this method was not in the consumed form of ATP; rather, it was added as a separate ATP source, and, in addition, the yield of conversion from AMP to ATP was very low (see S. Tochikura et al., ibid.). Therefore, even the approach which depended on the use of microbial glycolsis turned out to be negative with respect to the possibility of regenerating ATP from the particular type of AMP which is in the consumed form of ATP.

With a view to synthesizing a useful material by continuous consumption of ATP to AMP, the concept of a bioreactor has been proposed, and it has been strongly desired to complete a system employing such a bioreactor.

In order to meet this need, the present inventors previously made concerted efforts for regenerating ATP by conversion from AMP, which is the "lowest energy" metabolite of ATP. As a result, it was found that AMP could be rapidly converted to ATP with high yield by employing converging enzymes which were produced by microorganisms having an optimal-growth temperature range of 50° C. to 85° C. The present inventors also found that when ATP was regenerated from AMP with the AMP/ATP mixing ratio being controlled at a specified value, substantially 100% conversion of AMP to ATP was attainable. On the basis of these findings, the present inventors continued their studies and found that by linking (1) a reaction system for regenerating ATP from AMP with (2) a reaction system for synthesizing a physiologically active substance in the presence of ATP, the physiologically active substance of interest can be synthesized from AMP which is the decomposed form of ATP at the lowest energy level. Patent was applied for in respect of this invention in the United States of America (USSN 461,308) and under the European Patent Convention (EPC Publication No. 84975) and in Canada (Canadian Pat. No. 1,194,825).

However, it was later found that when a physiologically active substance was continuously synthesized for a prolonged period by the continuous-flow process wherein the two reaction systems were linked together within in a single reactor and the reactant solution was supplied at the one end of the reactor while the product (physiologically active substance) was withdrawn from the other end of the reactor, the reactor became plugged by precipitates and the supply of the reactant solution had to be suspended. In addition, when an enzyme immobilized on a water-insoluble support was employed, the precipitates had a tendency to deposit on the surface of the support and prevent contact between the reactant solution and the enzyme, with the result that the activity of the enzyme dropped so as to reduce the yield of the physiologically active substance.

G. M. Whitesides et al reported that they devised a reactor incorporating both a reaction system for regenerating ATP and a reaction system for synthesizing a physiologically active substance with the aid of ATP and that they synthesized the following substances: glucose 6-phosphate (*J. Org. Chem.*, Vol. 48, p. 3130 (1983)); dihydroxyacetone phosphate (ibid., Vol. 48, p. 3199 (1983)), creatine phosphate (ibid., Vol. 42, p. 4165 (1977)), NADP+ (J. Am. Chem. Soc., Vol. 106, p. 234 (1984)), ribulose 1,5-diphosphate (ibid., Vol. 102, p. 7938 (1980)) and glycerol 3-phosphate (ibid., Vol. 101, p. 5829 (1979)).

However, the productivity of the method of Whitesides et al. is very low, because a batch process is employed to produce the physiologically active substances. Furthermore, the reaction system for regenerating ATP in Whitesides et al. uses ADP, not AMP, as the starting material.

SUMMARY OF THE INVENTION

The principal object, therefore, of the present invention, is to provide a process for producing a physiologically active substance by performing in a continuous-flow fashion both a reaction for regenerating ATP from ADP or AMP and a reaction for synthesizing the physiologically active substance using ATP as an energy source.

With a view to attaining this object, the present inventors made extensive studies, and found that when no more than 30 mM of a divalent metal ion is present in the reactant solution, with the concentration of an adenosine-5'-phosphate (hereunder abbreviated as AXP) being held below the concentration of a precursor or precursors for the physiologically active substance of interest, the intended product can be produced by the continuous-flow process without forming any precipitate within the reactor. The present invention has been accomplished on the basis of this finding.

Therefore, the present invention is directed to a process for producing a physiologically active substance by a combined enzymatic method wherein a reactant solution containing a precursor or precursors for the physiologically active substance, AXP, and a divalent metal ion is supplied at one end of a reactor incorporating either of a combined enzymatic reaction system (a) or (b), wherein (a) is a reaction system including an enzyme for converting AMP to ADP, an enzyme for converting ADP to ATP, and an enzyme which catalyzes the synthesis of the physiologically active substance as it converts ATP to AMP; and (b) is a reaction system including an enzyme for converting ADP to ATP and an enzyme which catalyzes the synthesis of the physiologically active substance as it converts ATP to ADP, Wherein the concentration of the divalent metal ion supplied into the reactor is held at a level no higher than 30 mM while the concentration of the AXP is held below that of the precursor or precursors for the physiologically active substance, and the physiologically active substance produced is withdrawn from the other end of the reactor.

The process of the present invention offers a number of advantages, including the following: a physiologically active substance of interest can be synthesized in a continuous-flow bioreactor without forming any precipitate that will plug the reactor; the maneuverability of the reactor and the yield of the physiologically active substance of interest are appreciably increased; the cost of the starting materials is significantly reduced; and the reactor can be operated for a prolonged period without experiencing any deactivation of the enzyme or enzymes.

DETAILED DESCRIPTION OF PREFERRED EMBODIMENTS

Various enzymatic reactions may be employed in the present invention for the purpose of synthesizing physiologically active substances with the aid of ATP, which is used as an energy source as it is ultimately converted to AMP, and representative examples are listed below: a reaction for synthesizing acetyl-CoA (or acyl-CoA) from its precursors, acetic acid (or an aliphatic acid) and coenzyme A (CoA), in the presence of Acetyl-CoA synthetase (or acyl-CoA synthetase); a reaction for synthesizing D-pantothenic acid from its precursors, pantoic acid and $\beta$-alanine, in the presence of pantothenate synthetase; a reaction for synthesizing guanylic acid from its precursors, xanthylic acid and ammonia or glutamine, in the presence of quanylic acid synthetase; a reaction for synthesizing asparagine from its precursors, aspartic acid and ammonia, in the presence of aspartine synthetase; a reaction for synthesizing acyl CoA from its precursors, a carboxylic acid and CoA, in the presence of butyryl-CoA synthetase; a reaction for synthesizing o-D-alanyl-poly(ribitolphosphoric acid) from its precursors, D-alanine and poly(ribitolphosphoric acid), in the presence of D-alanyl-poly(ribitolphosphoric acid) synthetase; and a reaction for synthesizing $AND^+$ from its precursors, deamide $NAD^+$ and L-glutamine, in the presence of $NAD^+$ synthetase.

Enzymatic reactions may also be employed in the present invention for the purpose of synthesizing physiologically active substances with ATP being converted to ADP, and representative examples of such reactions include the following: a reaction for synthesizing $NADP^+$ from its precursor $NAD^+$ in the presence of $NAD^+$ kinase; a reaction for synthesizing dihydroxyacetonephosphate from its precursor dihydroxyacetone in the presence of glycerol kinase; a reaction for synthesizing glucose 6-phosphate from its precursor glucose in the presence of glucokinase; a reaction for synthesizing ribulose 1,5-bisphosphate from its precursor ribulose 5-phosphate in the presence of phosphoribulokinase; a reaction for synthesizing glycerol 3-phosphate from its precursor glycerol in the presence of glycerol kinase; a reaction for synthesizing creatine phosphate from its precursor creatine in the presence of creatine kinase; a reaction for synthesizing $\gamma$-glutamylcysteine from its precursors glutamic acid and cysteine in the presence of $\gamma$-glutamyl-cysteine synthetase; a reaction for synthesizing glutathione from its precursors $\gamma$-glutamyl cysteine and glycine in the presence of glutathione synthetase; a reaction for synthesizing AMP from its precursor adenosine in the presence of adenosine kinase; a reaction for synthesizing glutamine from its precursors glutamic acid and ammonia in the presence of glutamine synthetase; a reaction for synthesizing phosphocoline from its precursor choline in the presence of choline kinase; a reaction for synthesizing 4'-phosphopantothenic acid from its precursor pantothenic acid in the presence of pantothenate kinase; and a reaction for synthesizing phosphoenolpyruvic acid from its precursor pyruvic acid in the presence of pyruvate kinase.

In the systems of these reactions for synthesizing physiologically active substances, ATP is consumed to produce AMP or ADP. In accordance with the process of the present invention, AMP is converted to ATP with the aid of two enzymes, one for converting AMP to ADP and the other for converting ADP to ATP, while ADP as the consumed form of ATP is converted to ATP with the aid of an enzyme for converting ADP to ATP. Adenylate kinase may be used as an enzyme for catalyzing the conversion of AMP to ADP, with ATP being used as a phosphoric acid donor for AMP. Many enzymes may be used for catalyzing ADP-ATP conversion, such as acetate kinase, carbamate kinase, creatine kinase, 3-phosphoglycerate kinase, pyruvate kinase, and polyphosphate kinase. The phosphoric acid donors usable in this case include acetylphosphate, carbamylphosphate, creatine phosphate, 3-phosphoglycerolylphosphate, phosphoenolpyruvic acid and polyphosphoric acid. Acetate kinase may most advantageously be used in consideration of availability, the price of the usable phosphoric acid donor and the catalytic activity for conversion to ATP. Acetylphosphate is used as a phorphoric acid donor for acetate kinase. Acetylphosphate may be used in the form of a salt such as ammonium salt, potassium lithium salt, or sodium salt. A disodium salt is preferable for its ready availability.

In order to convert AMP to ATP in the present invention, adenylate kinase is preferably combined with acetate kinase, with ATP and acetylphosphate being used as phosphoric acid donors for the respective enzymes. However, since ATP as the final product of conversion can be recycled for use as the phosphoric acid donating ATP, only the acetylphosphate may be supplied as the phosphoric acid donor. Therefore, the combination of adenylate kinase and acetate kinase offers the advantage of an efficient process design.

While the use of converting enzymes allows ATP to be regenerated from the AMP or ADP produced in the course of synthesis of physiologically active substances, such converting enzymes are preferably those which originate from microorganisms having an optimum-growth temperature range of 50 to 85° C. Examples of such microorganisms include those of the general, Bacillus (*Bacillus stearothermophilus, Bacillus brevis, Bacillus coagulans, Bacillus thermoproteolyticus,* and *Bacillus acidocaldarius*), Clostridium, Thermoactinomyces, Acromobacter, Streptomyces, Micropolyspora, Thermus (e.g., *Thermus aquatious, Thermus athermophilus* and *Thermus flavus*), and Thermomicrobium. Mesophilic micro-organisms into which the genes of the above-listed micro-organisms have been incorporated may also be used to produce the converting enzymes suitable for use in the present invention. *Bacillus stearothermophilus* is particularly suitable as the source of adenylate kinase and acetate kinase. The two enzymes produced from this particular microorganism can be easily purified and have high specific activities. When the studies which eventually led to the accomplishment of the present invention first started, it was thought that the converting enzymes which were produced from microorganisms having optimum-growth temperatures within the range of 50 to 85° C. would be unsuitable for use in the regeneration of ATP at moderate temperatures. Surprisingly enough, however, these enzymes allowed AMP or ADP to be rapidly converted to ATP at moderate temperatures, and high conversion yields could be attained for an extended period of time. These advantages were far greater than those attained by enzymes produced from mesophilic microorganisms.

Any type of reactor may be employed in the present invention so long as it is capable of accommodating both the enzyme for synthesizing a physiologically active substance of interest and the enzyme or enzymes for reproducing ATP. The selection of a particular size and shape of the reactor employed will depend on the amount of each of the enzymes used, the concentration, pH and the supply rate of the reactant solution, and the reaction temperature. Reactors can generally be classified into two types according to shape: membrane reactors and column reactors. The membrane reactor best fits the purpose of synthesizing a low-molecular weight physiologically active substance. In this case, the enzyme which are large molecular substances can be used as they stay within the reactor. The low-molecular weight AXP which is supplied at one end of the reactor exits from the other end and may be returned to the reactor for reuse after it is separated from the physiologically active substance by a simple means such as ion-exchange chromatography. Even the need for this separation step can be eliminated by binding AXP to a water-soluble polymer with the aid of an appropriate spacer. Suitable water-soluble polymers include polysaccharides such as soluble dextran, vinyl polymer derivatives such as polyacrylamide and polyacrylic acid derivatives, and polyether derivatives such as polyethylene glycol derivatives.

The column reactor may be used for synthesizing any physiologically active substance. In this case, the enzymes are packed in the column after they are immobilized on support(s) by suitable techniques such as chemical bonding, entrapment, and adsorption. Appropriate supports include polysaccharide derivatives such as cellulose, dextran and agarose, vinyl polymer derivatives such as polystyrene, ethylene-maleic acid copolymers, and crosslinked polyacrylamide, polyamino acid or amide derivatives such as L-alanine/L-glutamic acid copolymer, and polyaspartic acid, and inorganic derivatives such as glass, alumina and hydroxyapatite. The AXP produced in the column reactor exits as an effluent whether it is bound to a water-soluble polymer or not, and may be returned to the reactor after it is separated from the physiologically active substance by a suitable technique. A water-soluble polymer bound AXP may be separated by simple membrane technology.

The reactant solution supplied to the membrane or column reactor typically contains a precursor or precursors for the physiologically active substance to be synthesized, the phosphoric acid donor for each of the enzymes employed, AXP, and appropriate divalent metal ions. Examples of suitable precursors and phosphoric acid donors are described above. For regenerating ATP from ADP, ADP may alone be used as AXP, but it often suffices to use only ATP or a mixture of ADP and ATP. Alternatively, the AXP recovered from the reaction solution after completion of the synthesis of the desired physiologically active substance may be recycled for another use. In the case of regenerating ATP from AMP, ATP alone may be used as AXP, but it often suffices to use only ADP, or a mixture of AMP and ATP, a mixture of AMP and ADP, a mixture of ADP and ATP, or a mixture of AMP, ADP, and ATP. Alternatively, the AXP recovered from the reaction solution after completion of the synthesis of the desired physiologically active substance may be recycled for reuse.

For the purposes of the present invention, the concentration (molar concentration) of AXP in the reactant solution must always be held below the concentration of the precursor or precursors for the intended physiologically active substance. As guide figures, the concentration of AXP is generally within the range of from 0.01 to 90%, preferably from 0.1 to 50%, and more preferably from 0.5 to 10%, of the concentration of the precursor or precursors.

In order to attain the desired product with high yield, the phosphoric acid based donor is advantageously used in an amount equal to or higher than that of the precursor of the physiologically active substance.

It is also necessary that the concentration of the divalent metal ion present in the reactant solution should be held at a value no higher than 30 mM, with a concentration which is no higher than 20 mM being preferable, for the purpose of ensuring more effective prevention of the formation of precipitates. Examples of the divalent metal ion that may be included in the reactant solution are magnesium, manganese, calcium, cobalt, cadmium, and barium ions.

In accordance with the present invention, a physiologically active substance of interest is produced by continuously supplying the reactant solution of the aforementioned composition into the reactor at one end of the reactor, while the product is withdrawn from the other end of the reactor. The reactant solution must be supplied with the concentrations of the components being controlled in such a manner that the aforementioned conditions are satisfied. Two typical methods for controlling the concentrations of the components in the reactant solution as it is continuously supplied into the reactor are as follows: a liquid mixture containing all necessary components in predetermined concentrations is continuously supplied into the reactor by a pump or other suitable means; alternatively, separate solutions of the components are fed into the reactor after their concentrations are adjusted to predetermined levels at the inlet port by controlling the supply rates of the respective solutions.

The following examples and comparative examples are provided for the purpose of further illustrating the present invention.

EXAMPLE 1

*Bacillus stearothermoohilus*-derived acetate kinase and adenylate kinase (Seikagaku Kogyo Co.) and yeast-derived acetyl-CoA synthetase(Boehringer Mannheim Co.) were separately immobilized on activated CH-Sepharose 4B (Pharmacia Fine Chemicals). Two thousand units of the immobilized acetate kinase, 200 units of the immobilizedadenylate kinase and 100 units of the immobilized acetyl-CoA synthetase were packed into a single column.

A reactant solution having 4 mM AMP, 1 mM ATP, 40 mM acetylphosphate, 25 mM potassium acetate and 25 mM reduced CoA lithium salt dissolved in 100 mM imidazole hydrochloride buffer solution (pH 7.5) containing 10 mM magnesium chloride was fed from above the column at a flow rate of 10 ml/hr while acetyl CoA was continuously with-drawn from the bottom of the column.

The withdrawn column effluent contained 18 mM acetyl CoA, and the yield of acetyl CoA remained substantially constant for the subsequent 15 hours. Throughout this experiment, the column temperature was held at 37° C.

COMPARATIVE EXAMPLE 1

The procedures of Example 1 were repeated except that the concentration of magnesium chloride in the reactant solution was increased to 50 mM. One hour after the start of the experiment, a precipitate formed in the column and the supply of the reactant solution into the column had to be suspended.

COMPARATIVE EXAMPLE 2

The procedures of Example 1 were repeated except that the concentrations of AMP and ATP in the reactant solution were increased to 40 mM and 10 mM, respectively. Three hours after the start of the experiment, a precipitate formed in the column and the supply of the reactant solution into the column had to be suspended.

EXAMPLE 2

*Bacillus stearothermophilus*-derived acetate kinase and adenylate kinase (500 and 200 units, respectively; Seikagaku Kogyo Co.) and yeast-derived acetyl-CoA synthetase (100 units; Boehringer Mannheim Co.) were dissolved in 100 mM imidazole hydrochloride buffer solution (pH 7.5) containing 10 mM magnesium chloride. The solution then was confined in a membrane reactor equipped with an ultrafiltration membrane (mol. wt. 30,000).

A reactant solution containing 4 mM AMP, 1 mM ATP, 40 mM acetylphosphate, 25 mM potassium acetate, and 25 mM reduced CoA lithium salt dissolved in 100 mM imidazole hydrochloride buffer solution (pH 7.5) containing 10 mM magnesium chloride was fed into the membrane reactor at a flow rate of 10 ml/hr, while acetyl CoA was withdrawn continuously from the other side of the reactor at the same rate.

The withdrawn effluent contained 17 mM acetyl CoA and the yield of acetyl CoA remained substantially constant for the subsequent 10 hours. Throughout this experiment, the reactor's temperature was held at 37° C.

EXAMPLE 3

Asparagine synthetase was obtained from *Lactobacillus arabinosus* ATCC 8014 and purified by ammonium sulfate fractionation and calcium phosphate gel filtration. The purified asparagine synthetase and *Bacillus stearothermophilus*-derived acetate kinase and adenylate kinase (Seikagaku Kogyo Co.) were separately immobilized on CNBr-activated Sepharose 4B (Pharmacia Fine Chemicals). Fifty units of the immobilized asparagine synthetase, 1,000 units of the immobilized acetate kinase, and 100 units of the immobilized adenylate kinase were packed into a single column.

A reactant solution having 20 mM ammonium chloride, 20 mM L-aspartic acid, 2 mM AMP, 0.5 mM ATP, and 30 mM acetylphosphate dissolved in 100 mM tris-HCl buffer solution (pH 7.5) containing 5 mM manganese chloride was fed from above the column at a flow rate of 5 ml/hr and L-asparagine was continuously withdrawn from the bottom of the column at the same rate.

The withdrawn column effluent contained 16 mM L-asparagine and the yield of asparagine remained substantially constant for the subsequent 12 hours. Throughout this experiment, the column temperature was held at 30° C.

COMPARATIVE EXAMPLE 3

The procedures of Example 3 were repeated except that the concentration of manganese chloride in the reactant solution was increased to 40 mM. Two hours after the start of the experiment, a precipitate formed in the column and the supply of the reactant solution had to be suspended.

COMPARATIVE EXAMPLE 4

The procedures of Example 3 were repeated except that the concentrations of AMP and ATP in the reactant were increased to 30 mM and 8 mM, respectively. Three hours after the start of the experiment, a precipitate formed in the column and the supply of the reactant solution had to be suspended.

EXAMPLE 4

*Bacillus Stearothermophilus*-derived acetate kinase and adenylate kinase (Seikagaku Kogyo Co.) and pantothenate synthetase as prepared by the method described in Methods in Enzymology, Vol. 2, p. 619 (1955), Academic Press, were separately immobilized on CNBr-activated Sepharose 4B (Pharmacia Fine Chemicals). A hundred units each of the immobilized acetate kinase, adenylate kinase and pantothenate synthetase were packed into a single column.

A reactant solution having 10 mM D-pantoic acid, 1 mM AMP, 1 mM ATP, 15 mM acetylphosphate and 10 mM β-alanine dissolved in 100 mM tris-HCl buffer solution (pH 8.0) containing 10 mM magnesium chloride and 100 mM potassium chloride was fed from above the column at a flow rate of 10 ml/hr while D-pantothenic acid was withdrawn continuously from the bottom at the same rate.

The withdrawn column effluent contained 7 mM D-pantothenic acid and the yield of D-pantothenic acid remained substantially the same for the subsequent 5 hours. Throughout the experiment, the column temperature was held at 30° C.

EXAMPLE 5

Bacillus stearothermophilus-derived acetate kinase and glucokinase (Seikagaku Kogyo Co.) were separately immobilized on CNBr-activated Sepharose 4B (Pharmacia Fine Chemicals). Twenty units each of the immobilized acetate kinase and glucokinase were packed into a single column.

A reactant solution having 10 mM glucose, 1 mM ADP, 15 mM dicodium salt of acetylphosphate and 20 mM mercaptoethanol dissolved in 100 mM tris-HCl buffer solution (pH 8.0) containing 5 mM magnesium chloride was fed from above column at a flow rate of 30 ml/hr while glucose 6-phosphate was continuously withdrawn from the bottom at the same rate.

The withdrawn column effluent contained 8.5 mM glucose 6-phosphate and the yield of glucose 6-phosphate remained substantially the same for the subsequent 20 hours. Throughout this experiment, the column temperature was held at 30° C.

COMPARATIVE EXAMPLE 5

The procedures of Example 5 were repeated except that the concentration of magnesium chloride in the reactant solution was increased to 40 mM. Two hours after the start of the experiment, a precipitate formed in the column and the supply of the reactant solution had to be stopped.

COMPARATIVE EXAMPLE 6

The procedures of Example 5 were repeated except that the concentration of ADP in the reactant solution was increased to 20 mM. Three hours after the start of the experiment, a precipitate formed in the column and the supply of the reactant solution had to be stopped.

EXAMPLE 6

A hundred and sixty units of immobilized acetate kinase and 130 units of immobilized glucokinase were packed into a single column as in Example 5.

A reactant solution having 100 mM glucose, 1 mM ADP, 120 mM disodium salt of acetylphosphate and 20 mM mercaptoethanol dissolved in 100 mM tris-HCl buffer solution (pH 8) containing 5 mM magnesium chloride was fed from above the column at a flow rate of 25 ml/hr while glucose 6-phosphate was continuously withdrawn from the bottom at the same rate.

The withdrawn column effluent contained 100 mM glucose 6-phosphate and the yield of glucose 6-phosphate remained substantially the same for the subsequent 40 hours. Throughout this experiment, the column temperature was held at 30° C.

COMPARATIVE EXAMPLE 7

The procedures of Example 6 were repeated except that the concentration of magnesium chloride in the reactant solution was increased to 50 mM. One hour after the start of the experiment, a precipitate formed in the column and the supply of the reactant solution into the column had to be suspended.

COMPARATIVE EXAMPLE 8

The procedures of Example 6 were repeated except that the concentration of ADP in the reactant solution was increased to 150 mM. Two hours after the start of the experiment, a precipitate formed in the column and the supply of the reactant solution into the column had to be suspended.

EXAMPLE 7

A hundred units of glutamine synthetase as derived from *Escherichia coli* in accordance with the method described in Methods in Enzymology, Vol. 17A, p. 910 (1970), Academic Press, and 100 units of *E. Coli*-derived acetate kinase (Boehringer Mannheim Co.) were dissolved in 100 mM tris-HCl buffer solution (pH 7.5) containing 20 mM magnesium chloride and the solution was confined in a membrane reactor equipped with an ultrafiltration membrane (mol. wt. 30,000).

A reactant solution having 50 mM ammonium chloride, 50 mM L-glutamic acid, 10 mM ADP, 80 mM disodium salt of acetylphosphate and 10 mM mercaptoethanol dissolved in 100 mM tris-HCl buffer solution (pH 7.5) containing 20 mM magnesium chloride was supplied into the reactor at a flow rate of 10 ml/hr while glutamine was continuously withdrawn from the other side at the same rate.

The effluent from the reactor contained 35 mM glutamine and the yield of glutamine remained substantially constant for the subsequent 6 hours.

EXAMPLE 8

Acetate kinase (Seikagaku Kogyo Co.) and choline kinase (Boehringer Mannheim Co.) were separately immobilized on CNBr-activated Sepharose 4B (Pharmacia Fine Chemicals). Five units each of the immobilized acetate kinase and choline kinase were packed into a single column.

A reactant solution having 5 mM choline, 1 mM ADP, 8 mM disodium salt of acetylphosphate and 5 mM dithiothreitol dissolved in 100 mM tris-HCl buffer solution (pH 8.5) containing 15 mM magnesium chloride was supplied from above the column at a flow rate of 5 ml/hr while o-phosphocoline containing effluent was withdrawn continuously from the bottom at the same rate.

The withdrawn column effluent contained 4.5 mM o-phosphocoline and the yield of o-phosphocoline remained substantially the same for the subsequent 8 hours. Throughout this experiment, the column temperature was held at 30° C.

While the invention has been described in detail and with reference to specific embodiments thereof, it will be apparent to one skilled in the art that various changes and modifications can be made therein without departing from the spirit and scope thereof.

What is claimed is:

1. A process for producing a physiologically active substance by a combined enzymatic method wherein a reactant solution containing a precursor or precursors for the physiologically active substance, an adenosine5'-phosphate, and a divalent metal ion is supplied at one end of a reactor incorporating either of a combined enzymatic reaction system (a) or (b), wherein
    (a) is a reaction system including an enzyme for converting adenosine-5'-monophosphate to adenosine-5'-diphosphate, an enzyme for converting adenosine-5'-diphosphate to adenosine-5'-triphosphate, and an enzyme which catalyzes the synthesis of the physiologically active substance as it converts adenosine-5'-triphosphate to adenosine-5'-monophosphate; and (b) is a reaction system including an enzyme for converting adenosine-5'-diphosphate to adenosine-5'-triphosphate and an enzyme which catalyzes the synthesis of the physiologically active substance as it converts adenosine-5'-triphosphate to adenosine-5'-diphosphate, wherein the concentration of the divalent metal ion supplied into the reactor is held at a level no higher than 30 mM while the concentration of the adenosine-5'-phosphate is held below that of the precursor or precursors for the physiologically active substance, and the physiologically active substance produced is withdrawn from the other end of the reactor.

2. A process for producing a physiologically active substance as in claim 1, wherein the concentration of the divalent metal ion supplied into the reactor is held at the level no higher than 20 mM.

3. A process for producing a physiologically active substance as in claim 1, wherein the concentration of adenosine-5'-phosphate is from 0.1 to 50 mole% of the concentration of the precursor or precursors for the physiologically active substance.

4. A process for producing a physiologically active substance as in claim 1, wherein the concentration of adenosine-5'-phosphate is from 0.5 to 10 mole% of the concentration of the precursor or precursors for the physiologically active substance.

5. A process for producing a physiologically active substance as in claim 2, wherein the concentration of adenosine-5'-phosphate is from 0.1 to 50 mole% of the concentration of the precursor or precursors for the physiologically active substance.

6. A process for producing a physiologically active substance as in claim 2, wherein the concentration of adenosine-5'-phosphate is from 0.5 to 10 mole% of the concentration of the precursor or precursors for the physiologically active substance.

* * * * *